United States Patent

Krüger et al.

[11] Patent Number: 5,166,144
[45] Date of Patent: Nov. 24, 1992

[54] O-HALOGENOCYCLOBUTYL S-ALKYL (DI)THIOPHOSPHORIC ACID ESTER-AMIDES AND THEIR USE AS AGENTS FOR COMBATING PESTS

[75] Inventors: Bernd-Wieland Krüger, Bergisch Gladbach; Dietmar Bielefeldt, Ratingen-Hösel; Karl-R. Gassen, Odenthal; Jürgen Hartwig, Leverkusen; Wilhelm Stendel, Wuppertal; Christoph Erdelen, Leichlingen, all of Fed. Rep. of Germany

[73] Assignee: Bayer Aktiengesellschaft, Leverkusen, Fed. Rep. of Germany

[21] Appl. No.: 854,183

[22] Filed: Mar. 20, 1992

[30] Foreign Application Priority Data

Mar. 30, 1991 [DE] Fed. Rep. of Germany ....... 4110485

[51] Int. Cl.$^5$ .................. A01N 57/28; C07F 9/26; C07F 9/24; C07F 9/20
[52] U.S. Cl. .................. 514/120; 514/129; 514/137; 558/178; 558/185; 558/199; 558/202
[58] Field of Search .............. 558/178, 199, 202; 514/120, 137

[56] References Cited

U.S. PATENT DOCUMENTS 4,973,583 11/1990 Krüger et al. .............. 514/141

Primary Examiner—Mary C. Lee
Assistant Examiner—Michael G. Ambrose
Attorney, Agent, or Firm—Sprung Horn Kramer & Woods

[57] ABSTRACT

The invention relates to new O-halogenocyclobutyl S-alkyl (di)thiophosphoric acid ester-amides of the general formula (I)

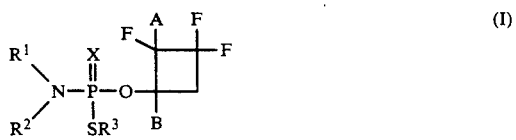

in which
A represents fluorine or chlorine,
B represents hydrogen or alkyl,
X represents oxygen or sulphur,
$R^1$ represents hydrogen, alkyl, —COH (formyl) or —CO-alkyl (acyl) which is optionally substituted by halogen,
$R^2$ represents hydrogen or alkyl, and
$R^3$ represents alkyl or alkoxyalkyl,
which can be used as agents for combating pests.

8 Claims, No Drawings

O-HALOGENOCYCLOBUTYL S-ALKYL (DI)THIOPHOSPHORIC ACID ESTER-AMIDES AND THEIR USE AS AGENTS FOR COMBATING PESTS

The invention relates to new O-halogenocyclobutyl S-alkyl (di)thiophosphoric acid ester-amides, several processes for their preparation and their use as agents for combating pests, in particular as insecticides, acaricides and nematicides.

It is already known that certain O-halogenocyclobutyl S-(alkyl) (di)thiophosphoric acid esters, such as, for example, thiophosphoric acid S-propyl P-ethyl O-(3,3,2-trifluoro-2-chloro-cyclobutyl triester, can be used for combating pests (compare U.S. Pat. Specification No. 4,973,583).

However, the insecticidal, acaricidal and nematicidal action of the known compounds is not always completely satisfactory for all problem areas, especially in the case of low active compound concentrations and when low amounts are used.

New O-halogenocyclobutyl S-alkyl (di)thiophosphoric acid ester-amides of the general formula (I)

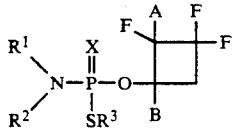
(I)

in which
A represents fluorine or chlorine,
B represents hydrogen or alkyl,
X represents oxygen or sulphur,
$R^1$ represents hydrogen, alkyl, —COH (formyl) or —CO-alkyl (acyl) which is optionally substituted by halogen,
$R^2$ represents hydrogen or alkyl and
$R^3$ represents alkyl or alkoxyalkyl,
have now been found.

Where appropriate, the compounds of the formula (I) have one or more centres of asymmetry. They can therefore exist in various isomer forms, which can be obtained in different proportions. The invention relates both to the isomer mixtures and to the individual isomers.

For simplicity, however, compounds of the formula (I) will always be referred to below, although both the pure compounds and, where appropriate, also mixtures with various contents of isomeric compounds are meant.

It has furthermore been found that the new O-halogenocyclobutyl S-alkyl (di)thiophosphoric acid ester-amides of the formula (I) are obtained by a process in which
a) thio- or dithiophosphoric acid ester-amides of the formula (II)

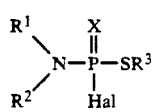
(II)

in which
$R^1$, $R^2$, $R^3$ and X have the abovementioned meaning and Hal represents halogen, are reacted with cyclobutanol derivatives of the formula (III)

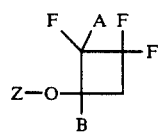
(III)

in which
A and B have the abovementioned meaning and
Z represents hydrogen or one equivalent of an alkali metal ion, if appropriate in the presence of diluents and if appropriate in the presence of bases,
or by a process in which
b) in a first reaction step, acid halides of the formula (IV)

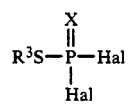
(IV)

in which
X, $R^3$ and Hal have the abovementioned meaning,
are reacted with compounds of the formula

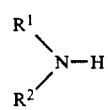
(V)

in which
$R^1$ and $R^2$ have the abovementioned meaning,
if appropriate in the presence of solvents and if appropriate in the presence of bases, and the resulting product of the formula (II) is reacted in a subsequent reaction step with cyclobutanol derivatives of the formula (III), if appropriate in the presence of diluents and if appropriate in the presence of bases,
or by a process in which
c) in a first reaction step, compounds of the formula (VI)

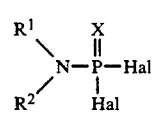
(VI)

in which
$R^1$, $R^2$, X and Hal have the abovementioned meaninq,
are reacted with compounds of the formula (III), if appropriate in the presence of diluents and if appropriate in the presence of bases, and the resulting compounds of the formula (VII)

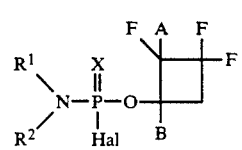
(VII)

in which
$R^1$, $R^2$, A, B, X and Hal have the abovementioned meaning, are reacted in a second reaction step with compounds of the formulae (VIIIa) or (VIIIb)

Z¹—SH     (VIIIa)

or (Z¹)₂S     (VIIIb)

in which
Z¹ represents one equivalent of an alkali metal ion,
if appropriate in the presence of a diluent, and the resulting compounds of the formula (IX)

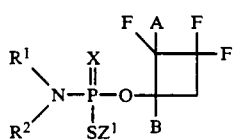     (IX)

in which
R¹, R², A, B, X and Z¹ have the abovementioned meaning,
are reacted with compounds of the formula (X)

R³—Hal     (X)

in which
R³ and Hal have the abovementioned meaning,
if appropriate in the presence of a diluent and if appropriate in the presence of a base, or by a process in which d) in a first step, compounds of the formula (IV) are reacted with compounds of the formula (III), if appropriate in the presence of diluents and if appropriate in the presence of bases, and in a second step, the resulting compounds of the formula (XI)

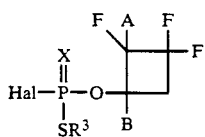     (XI)

in which
A, B, X, R³ and Hal have the abovementioned meaning, are reacted with compounds of the formula (V), if appropriate in the presence of a diluent and if appropriate in the presence of a base,
or by a process in which e) to prepare compounds of the formula (I) in which R² represents formyl or acyl, compounds of the formula (XII)

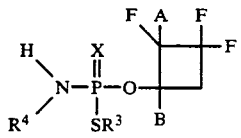     (XII)

in which
A, B, X and R³ have the abovementioned meaning and R⁴ represents hydrogen or alkyl,
are reacted with compounds of the formula (XIII)

R⁵—CO—Y     (XIII)

in which
R⁵ represents hydrogen or alkyl which is optionally substituted by halogen and
Y represents halogen or another group which cleaves during acylation reactions,
if appropriate in the presence of a diluent or if appropriate in the presence of a base.

It has furthermore been found that the new compounds of the general formula (I) have a very good activity as agents for combating pests, in particular against undesirable arthropods, such as insects and spider mites, and against nematodes. The new compounds thus represent a useful enrichment of the art.

In the general formulae, the radical

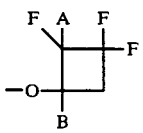

denotes the cyclobutyl radical of the formula

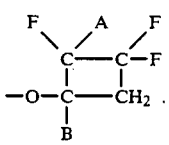

The radicals mentioned in the general formulae are explained as follows:

Alkyl denotes straight-chain or branched alkyl having preferably 1 to 6, particularly preferably 1 to 4 and especially preferably 1 to 3 carbon atoms, methyl, ethyl, n- and i-propyl and n-, i-, sec- and t-butyl being mentioned specifically.

The explanations given for alkyl apply accordingly to the alkyl parts of —CO-alkyl and alkoxyalkyl. CO-alkyl which should be emphasised specifically is —CO—C₁-C₄-alkyl, and in particular —COCH₃ and —COC₂H₅. Alkoxyalkyl which should be emphasised specifically is C₁-C₄-alkoxy -C₁-C₂-alkyl, in particular methoxymethyl, ethoxymethyl, methoxyethyl and ethoxyethyl.

CO-alkyl can be substituted by one or more, preferably 1 to 5, in particular 1 to 3, identical or different halogen atoms, and the COCF₃ group should be emphasised specifically. The same applies accordingly to the alkyl group R⁵.

Halogen denotes fluorine, chlorine, bromine or iodine, preferably fluorine, bromine or iodine, particularly preferably chlorine or bromine and especially preferably chlorine. In the case of CO-alkyl (or alkyl R⁵) which is substituted by halogen, halogen preferably denotes fluorine, chlorine and/or bromine, particularly preferably chlorine and/or fluorine and especially preferably fluorine.

Preferred alkali metal ions are lithium, sodium and potassium ions.

B preferably represents hydrogen or C₁-C₆-alkyl.
R¹ preferably represents hydrogen, C₁-C₆-alkyl, —COH or —CO—C₁-C₆-alkyl which is optionally substituted by halogen.
R² preferably represents hydrogen or C₁-C₆-alkyl.
R³ preferably represents C₁-C₆-alkyl or C₁-C₆-alkoxy-C₁-C₆-alkyl.

Compounds of the formula (I) which are preferred according to the invention are those in which a combination of these meanings listed above as preferred is present.

B particularly preferably represents hydrogen or $C_1-C_4$-alkyl.

$R^1$ particularly preferably represents hydrogen, $C_1-C_4$-alkyl, —COH or —CO—$C_1-C_4$-alkyl which is substituted by halogen (preferably fluorine).

$R^2$ particularly preferably represents hydrogen or $C_1C_4$-alkyl.

$R^3$ particularly preferably represents $C_1-C_4$-alkyl or $C_1-C_4$-alkoxy-$C_1-C_4$-alkyl.

Compounds of the formula (I) which are particularly preferred according to the invention are those in which a combination of these meanings listed above as particularly preferred is present.

B especially preferably represents hydrogen.

$R^1$ especially preferably represents hydrogen.

$R^2$ especially preferably represents methyl or ethyl (in particular ethyl).

$R^3$ especially preferably represents $C_3-C_4$-alkyl.

Compounds of the formula (I) which are especially preferred according to the invention are those in which a combination of these meanin9s listed above as especially preferred is present.

Compounds of the formula (I) which are emphasised in particular according to the invention are those in which X represents oxygen.

Compounds of the formula (I) which are emphasised in particular according to the invention are those in which B represents hydrogen or methyl, in particular hydrogen.

The radical definitions or explanations mentioned above generally or mentioned in preferred ranges apply accordingly to the end products and to the starting subtances and intermediate products. These radical definitions can be combined with one another as desired, that is to say also between the particular preferred ranges.

The following O-halogenocyclobutyl-S-alkyl-(di)thiophosphoric acid ester-amides of the general formula (I) may be mentioned as specific examples, in addition to the compounds mentioned in the preparation examples:

| $R^1$ | $R^2$ | $R^3$ | A | B | X |
|---|---|---|---|---|---|
| H | H | n-$C_3H_7$ | Cl | H | S |
| H | H | i-$C_3H_7$ | Cl | H | S |
| H | H | s-$C_4H_9$ | Cl | H | S |
| $CH_3$ | H | n-$C_3H_7$ | Cl | H | O |
| $CH_3$ | $CH_3$ | i-$C_3H_7$ | Cl | H | O |
| H | H | n-$C_3H_7$ | F | H | O |
| H | H | i-$C_3H_7$ | F | H | O |
| $C_2H_5$ | H | i-$C_3H_7$ | F | H | O |
| $CH_3$ | $CH_3$ | n-$C_3H_7$ | F | H | O |
| $CH_3$ | $C_2H_5$ | n-$C_3H_7$ | F | H | O |

The phosphoric acid derivatives of the general formulae (II), (IV) and (VI) used as starting substances are known or can be prepared by known processes (compare "Methoden der organischen Chemie [Methods of Organic Chemistry]" (Houben-Weyl) Volume E2, 1982, Georg Thieme Verlag Stuttgart, New York, page 300 et seq. and page 487 et seq.).

The starting substances of the formulae (VII), (IX) and (XI) are new and form part of the present invention. They are obtained in accordance with the first reaction step of process variants c) or the second step of process variants c) and d). They are isolated and purified by the customary methods, for example by distillation or chromatography.

The new compounds of the 9eneral formulae (VII), (IX) and (XI) can be summarised under the 9eneral formula (XIV)

in which

A, B and X have the abovementioned meaning, $R^6$ sents halogen, —$SZ^1$ or —$SR^3$, in which $R^3$ has the abovementioned meaning and $Z^1$ represents one equivalent of an alkali metal ion, and $R^7$ represents halogen or

wherein $R^1$ and $R^2$ have the abovementioned meaning, with the provisos that (a) $R^6$ and $R^7$ do not simultaneously denote halogen and (b) $R^6$ represents halogen or $SZ^1$ if $R^7$ represents $R^1R^2N$.

The cyclobutanol derivatives of the formula (III) used as starting substances are known from U.S. Pat. Specification No. 4,973,583, or they can be prepared by known methods (compare, for example, R. N. Hazeldine et al., J. Fluorine Chemistry, 28, 291 (1985); H. Gilman et al., J. Am. Chem Soc; 70, 128 (1948); L. S. Bogut Iarskaya et al., Zh. Org. Khim., 9, 296 (1973); and E. D. Bergmann et al., J. Chem. Soc., 1958, 2259).

The other starting substances to be used according to the invention are known or can be obtained by generally known methods and processes.

Possible diluents for process variant a) according to the invention are virtually all the inert organic diluents and their mixtures. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, cycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methylpyrrolidone, and dimethyl sulphoxide, tetramethylene sulphone and hexamethylphosphoric acid triamide.

For carrying out process variants a) according to the invention, 1 to 2 mol, preferably 1.0 to 1.8 mol, of cyclobutanol derivative of the formula (III) are employed per mol of phosphorus derivative of the formula (II).

Diluents which can be used for process variants b), c), d) and e) according to the invention are virtually all the inert organic diluents.

The diluents which have been mentioned in connection with the description of process variants a) according to the invention are preferably used.

If appropriate, process variants a), b), c), d) and e) can be carried out in the presence of bases. Bases which can be used are all the customary bases. Particularly preferred bases are alkali metal carbonates and alcoholates, such as sodium carbonate, potassium carbonate, sodium methylate or ethylate and potassium methylate or ethylate, and furthermore aliphatic, aromatic or heterocyclic amines, for example collidine, triethylamine, trimethylamine, dimethylaniline, dimethylbenzylamine, tetraethylenediamine (DABCO) and pyridine. The bases are preferably added in an amount which is necessary to trap the hydrogen halid formed.

Process variants a), b), c), d) and e) according to the invention are in general carried out at temperatures between $-70°$ C. and $+150°$ C. The range between $-40°$ C. and $110°$ C. is preferred.

The reactions are in general carried out under normal pressure.

To carry out process variant b) according to the invention, 1 to 1.6 mol, preferably 1 to 1.4 mol, of the amine of the formula (V) and 1 to 2, preferably 1 to 1.8 mol of the cyclobutanol derivative of the formula (III) are employed per mol of the compound of the formula (IV).

For carrying out process variant c) according to the invention, 1 to 1.6 mol, preferably 1 to 1.4 mol, of the cyclobutanol derivative of the formula (III), 1 to 2, preferably 1 to 1.8 mol, of the compounds of the formula (VIIIa) or (VIIIb) and 1 to 2, preferably 1 to 1.8 mol of the alkyl halides of the formula (X) are employed per mol of the compound of the formula (VI).

For carrying out process variant d) according to the invention, 1 to 2 mol, preferably 1 to 1.3 mol, of the cyclobutanol derivative of the formula (III) are employed per mol of the compound of the formula (IV) and, for the second reaction step, 1 to 4 mol, preferably 1 to 1.5 mol, of the amine of the formula (V) are employed per mol of the monohalide of the formula (XI).

To obtain the compounds of the formula (I) in which $R^1$ represents acyl or formyl, 1 to 2, preferably 1 to 1.3 mol, of the compound of the formula (XIII) are employed per mol of the phosphorus compound of the formula (XII) in process variant e).

The compounds according to the invention are worked up by customary methods. In some cases, the new compounds are obtained in the form of oils, some of which cannot be distilled without decomposition, but are freed from the last volatile contents by so-called "incipient distillation", that is to say by prolonged heating to moderately elevated temperatures under reduced pressure, and are purified in this manner. They are characterised by their refractive index.

The active compounds according to the invention are suitable for combating animal pests, in particular insects, arachnids and nematodes, encountered in agriculture, in forestry, in the protection of stored products and of materials, and in the hygiene sector, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulcare* and *Porcellio scaber*. From the order of the Diplopoda, for example, *Blaniulus guttulatus*.

From the order of the Chilopoda, for example, *Geophilus carpophagus* and *Scutigera* spec. From the order of the Symphyla, for example, *Scutigereella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella oermanica, Acheta domesticus,* Gryllotalpa spp., *Locusta migratoria* migratorioides, *Melanoplus differentialis* and *Schistocerca gregaria*. From the order of the Dermaptera, for example, *Forficula auricularia*.

From the order of the Isoptera, for example, Reticulitermes spp..

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp. From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blncardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordious, Ceutnorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp..

From the order of the Arachnica, for example, *Scorpio maurus* and *Latrodectus mactans*.

From the order of the Acarina, for example, *Acarus siro*, Argas spp., Ornithodoros spp., *Dermanyssus gallinae*, , *Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp..

The phytoparasitic nematodes include Pratylenchus spp., *Radopholus similus, Ditylenchus dipsaci, Tylenchulus semipenetrans*, Heterodera spp., Meloidogyne spp., Aphelenchoides spp., Longidorus spp., Xiphenema spp. and Trichodorus spp..

The active compounds of the formula (I) according to the invention are distinguished by a high insecticidal, acaricidal and above all nematicidal activity. They can be used in particular against insects which damage plants, such as, for example, against the caterpillars of the diamond-back moth (*Plutella maculipennis*) or against the larvae of the mustard beetle (*Phaedon cochleariae*), and also against mites which damage plants, such as, for example, against the common spider mite (*Tetranychus urticae*). In addition, they are outstandingly suitable for combating soil insects and nematodes and can be used, for example, combating *Phorbia antiqua* maggots or nematodes of the genus *Meloidogyne incognita*. A good root-systemic action, for example against *Phaedon cochleariae* larvae, is also to be emphasised. The nematicidal action of the active compounds according to the invention can also be confirmed in the in vitro test, for example against nematodes of the genus *Caenorhabditis elegans* living as endoparasites.

In addition, the active compounds of the formula (I) according to the invention have a high action against hygiene pests and stored product pests and can be employed, for example, for combating the oriental cockroach (*Blatta orientalis*) or for combating the common grain weevil (*Sitophilus granarius*). The active compounds according to the invention can moreover be employed with particularly good success for combating warm-blooded pests living as parasites (both ecto- and endoparasites), such as, for example, against the larvae of the sheep maggot fly (*Lucilia cuprina*), against cattle ticks (*Boophilus microplus*), against scab mites (*Psoroptes ovis*), against stable flies (*Stomoxys calcitrans*) or against the autumn fly (*Musca autumnalis*).

In addition, the active compounds of the formula (I) according to the invention also have a good fungicidal activity and can be employed for combating plant diseases, such as, for example, against the rice spot disease causative organism (*Pyricularia oryzae*) or against scab and Botrytis causative organisms.

When applied in appropriate amounts, the active compounds of the formula (I) according to the invention moreover have a herbicidal activity.

The active compounds according to the invention can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

Depending on their particular physical and/or chemical properties, the active compounds can be converted into customary formulations, such as solutions, emulsions, suspensions, powders, foams, pastes, granules, aerosols, natural and synthetic materials impregnated with active compound, very fine capsules in polymeric substances and in coating compositions for seed, and furthermore formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. A liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye stuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored product pests, the active compounds are distinguished by an excellent residual action on wood and clay as well as by a good stability to alkali on limed substrates.

The active compounds according to the invention are also suitable for combating insects, mites, ticks etc. in the sector of animal keeping and cattle breeding, where better results, for example higher milk production, greater weight, more attractive animal pelt, longer life etc., can be achieved by combating the pests.

The application of the active compounds according to the invention occurs in this sector in a known fashion, such as by external application in the form of, for example, dipping, spraying, pouring-on, spotting-on and dusting. The preparation of the compounds according to the invention will be illustrated with the aid of the following examples.

EXAMPLE 1

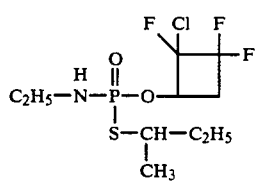

10.5 g (0.05 mol) of thiophosphoric acid dichloride S-(1-methylpropyl) ester are dissolved in 300 ml of hexane, 8 ml (0.057 mol) of triethylamine is first added at between 0 and −5° C., and 8.1 g (0.05 mol) of 2-chloro-2,3,3-trifluorocyclobutan-1-ol, dissolved in 25 ml of methylene chloride, are then added. The mixture is stirred at 20° C. for 2 hours and 10 g (0.22 mol) of ethylamine are then added dropwise to the reaction mixture at 20° C. To bring the reaction to completion, the mixture is stirred at 50°-60° C. for 24 h, the solid is filtered off and the solvent is distilled off under reduced pressure. The residue is then further purified by filtration over silica gel (cyclohexane : ethyl acetate =7:3 parts by volume). After the solvent has been distilled off, 6.0 g (35% of theory) of thiophosphoric acid 0-(2-chloro-2,3,3-trifluorocyclobutyl) S-(1-methylpropyl) diester N-ethylamide of refractive index $n_D^{30} = 1.4695$ are obtained.

EXAMPLE 2

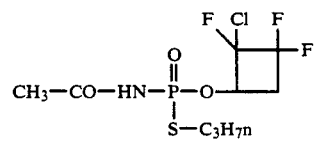

3.3 g of thiophosphoric acid O-(2-chloro-2,3,3-trifluorocyclobutyl ester)-amide S-propyl ester (0.01 mol) are dissolved in 50 ml of pyridine, and 0.5 g of 4-pyrrolidinopyridine (3.4 mmol) and 2 g of acetic anhydride (0.02 mol) are then added at 20° C. The reaction solution is stirred at 40° C. for 24 hours, poured onto water, extracted with methylene chloride and dried with magnesium sulphate and the solvent is distilled off under reduced pressure. The residue is then further purified by filtration over silica gel (mobile phase toluene : ethyl acetate=7:3 parts by volume). After the solvent has been disilled off, 2 g (59% of theory) of thiophosphoric acid N-acetyl-amide O-(2-chloro-2,3,3-trifluorocyclobutyl) S-n-propyl ester of refractive index $n_D^{20} = 1.4725$ are obtained.

EXAMPLE 3

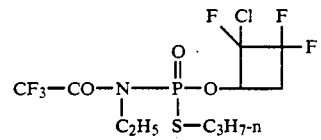

3 g (80% of theory) of thiophosphoric acid N-2,2,2-trifluoroacetyl-N-ethylamide O-(2-chloro-2,3,3-trifluorocyclobutyl) S-propyl ester of boiling point b.p.$_{0.2}$=95°-100° C./bulb tube oven are obtained analogously from 3.3 g of thiophosphoric acid O-(2-chloro-2,3,3-trifluorocyclobutyl ester) N-ethylamide S-propyl ester and 5 g of trifluoroacetic anhydride.

The compounds of the formula (I)

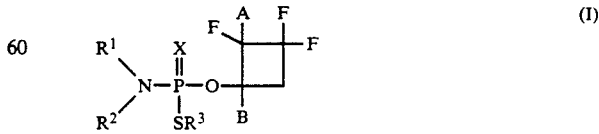

listed in the following Table 1 are obtained in an analogous manner, taking into consideration the statements in the description on the process variants according to the invention:

| Example No. | R¹ | R² | R³ | A | B | X | Refractive index $n_D^{20}$ or m.p. °C. |
|---|---|---|---|---|---|---|---|
| 4 | C₂H₅ | H | n-C₃H₇ | Cl | H | O | 1.4641 |
| 5 | n-C₃H₇ | H | n-C₃H₇ | Cl | H | O | 1.4636 |
| 6 | H | H | n-C₃H₇ | Cl | H | O | 1.4730 |
| 7 | CH₃ | CH₃ | n-C₃H₇ | Cl | H | O | 1.4583 |
| 8 | CH₃ | C₂H₅ | n-C₃H₇ | Cl | H | O | 1.4581 |
| 9 | i-C₃H₇ | H | n-C₃H₇ | Cl | H | O | 1.4606 |
| 10 | H | H | CH₃ | F | H | O | m.p. 48 |
| 11 | H | C₂H₅ | CH(CH₃)C₂H₅ | F | H | O | 1.4396 |
| 12 | H | C₂H₅ | n-C₃H₇ | F | H | O | 1.4385 |
| 13 | H | C₂H₅ | CH(CH₃)C₂H₅ | F | H | S | |
| 14 | H | C₂H₅ | n-C₃H₇ | F | H | S | |
| 15 | H | C₂H₅ | CH(CH₃)C₂H₅ | Cl | H | S | |
| 16 | H | C₂H₅ | n-C₃H₇ | Cl | H | S | |

The biological action of the compounds according to the invention will be illustrated with the aid of the following examples.

EXAMPLE A

Plutella test
Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the diamond-back moth (Plutella maculipennis) while the leaves are still moist.

After the specified periods of time, the destruction in % is determined. 100% means that all the caterpillars have been killed; 0% means that none of the caterpillars have been killed.

In this test, for example, the compounds of Preparation Examples 4, 8 and 9 showed a 100% destruction after 3 days at a concentration of, for example, 0.01%.

EXAMPLE B

Tetranychus test (resistant)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested with all the development stages of the common spider mite or two-spotted spider mite (Tetranychus urticae) are treated by being dipped into the preparation of the active compound of the desired concentration.

After the specified periods of time, the destruction in is determined. 100% means that all the spider mites have been killed; 0% means that none of the spider mites have been killed.

In this test, for example, the compounds of Preparation Examples 1, 6, 7, 8 and 9 showed a 90% destruction at an active compound concentration of, for example, 0.1% and 2 days.

EXAMPLE C

Critical concentration test/soil insects
Test insect: in the soil
Solvent: *Phorbia antiqua larvae* 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/1), being decisive. The soil is transferred into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compound of Preparation Example 4 showed a degree of effectiveness of 100% at an active compound concentration of, for example, 20 ppm.

EXAMPLE D

Critical concentration test / nematodes
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount by weight of active compound per unit volume of soil, which is given in ppm, being decisive. The treated soil is transferred into pots and these are planted with lettuce and the pots are kept at a greenhouse temperature of 27° C.

After 4 weeks, the lettuce roots are inspected for attack by nematodes (root balls) and the degree of effectiveness of the active compound is determined in %. The degree of effectiveness is 100% if attack is avoided completely, and is 0% if attack is just as high as in the case of the control plants in untreated soil infested in the same manner.

In this test, for example, the compounds of Preparation Examples 4, 5, 8 and 9 showed a degree of effectiveness of 100% at a concentration of, for example, 20 ppm.

EXAMPLE E

Critical concentration test
Test nematode: *Globodera rostochiensis*
Solvent: 3 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount by weight of active compound per unit volume of soil, which is given in ppm, being decisive. The treated soil is transferred into pots and these are planted with potatoes and the pots are kept at a greenhouse temperature of 18° C.

After six weeks, the potato roots are examined for cysts and the degree of effectiveness of the active compound is determined in %. The degree of effectiveness is 100% if attack is avoided completely, and is 0% if attack is just as high as in the case of the control plants in untreated soil infested in the same manner.

In this test, for example, the compounds of Preparation Examples 4, 5 and 8 showed a degree of effectiveness of 100% at a concentration of, for example, 20 ppm.

EXAMPLE F

Fly test
Test insects: *Musca domestica*, strain WHO(N)
Solvent: 35 parts by weight of ethylene glycol monomethyl ether 35 parts by weight of nonylphenol polyglycol ether To produce a suitable formulation, 3 parts by weight of active compound are mixed with 7 parts of the above-mentioned solvent-emulsifier mixture, and the emulsion concentrate thus obtained is diluted with water to the particular desired concentration.

2 ml of this preparation of active compound are pipetted onto filter paper discs ($\phi$9.5 cm) in Petri dishes of appropriate size. After the filter discs have dried, 25 test insects are transferred into the Petri dishes and covered.

After 6 hours, the effectiveness of the active compound preparation is determined. The effectiveness is expressed in %. 100% means that all the flies have been killed; 0% means that none of the flies have been killed.

In this test, for example, the compounds of Preparation Examples 4 and 8 showed a 100% destruction at an active compound concentration of, for example, 1000 ppm.

EXAMPLE G

Grain weevil test
Test animals: *Sitophilus granarius*
Solvent: 35 parts by weight of ethylene glycol monomethyl ether 35 parts by weight of nonylphenol polyglycol ether To produce a suitable formulation, 3 parts by weight of active compound are mixed with 7 parts of the above-mentioned solvent-emulsifier mixture, and the emulsion concentrate thus obtained is diluted with water to the particular desired concentration.

2 ml of this preparation of active compound are pipetted onto filter paper discs ($\phi$9.5 cm) in Petri dishes of appropriate size. After the filter discs have dried, 25 test insects are transferred into the Petri dishes and covered.

After 3 days, the effectiveness of the active compound preparation is determined. The effectiveness is expressed in %. 100% means that all the grain weevils have been killed; 0% means that none of the grain weevils have been killed.

In this test, for example, the compounds of Preparation Examples 1, 4, 5 and 8 showed a 100% destruction at an active compound concentration of, for example, 1000 ppm.

EXAMPLE H $LD_{100}$ test
Test insects: *Blattella germanica* and/or *Periplaneta americana* and *Sitophilus granarius*
Solvent: 35 parts by weight of ethylene glycol monomethyl ether 35 parts by weight of nonylphenol polyglycol ether To produce a suitable formulation, 3 parts by weight of active compound are mixed with 7 parts of the abovementioned solvent-emulsifier mixture, and the emulsion concentrate thus obtained is diluted with water to the particular desired concentration.

2 ml of this preparation of active compound are pipetted onto filter paper discs ($\phi$9.5 cm) in Petri dishes of appropriate size. After the filter discs have dried, 5 test insects in the case of B. germanica or P. americana and about 30 test animals in the case of S. granarius are transferred into the Petri dishes and covered.

In this test, 100% destruction resulted at an active compound concentration of, for example, 1000 ppm in the case of

*Blattella garmanica*: Preparation Examples 2, 3, 5 and 6

*Periplaneta americana*: Preparation Example 1
*Sitophilus granarius*: Preparation Example 1, 2, 3 and 6

EXAMPLE J

Blowfly larvae test
Test animals *Lucilia cuprina* larvae
Emulsifier: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture, and the emulsion concentrate thus obtained is diluted with water to the particular desired concentration.

About 20 Lucilia cuprina res. larvae are introduced into a test tube which contains approx. 1 cm$^3$ of horse meat 1 and 0.5 ml of the preparation of active compound. After 24 hours, the effectiveness of the active compound preparation is determined. 100% means that all the blowfly larvae have been killed; 0% means that none of the blowfly larvae have been killed.

In this test, for example, the compounds of Preparation Examples 1, 4, 5, 6, 7, 8 and 10 showed a 100% destruction at an active compound concentration of, for example, 1000 ppm.

We claim:

1. An O-halogenocyclobutyl S-alkyl (di)thiophosphoric acid ester-amide of the general formula (I)

$$\begin{array}{c} R^1 \\ \diagdown \\ N-P-O \\ \diagup \\ R^2 \quad SR^3 \end{array} \begin{array}{c} A \quad F \\ \diagup \\ X \\ \diagdown \\ B \end{array} F \quad (I)$$

in which
A represents fluorine or chlorine,
B represents hydrogen or alkyl,
X represents oxygen or sulphur,
$R^1$ represents hydrogen, alkyl, —COH (formyl) or —CO-alkyl (acyl) which is optionally substituted by halogen,
$R^2$ represent hydrogen or alkly and
$R^3$ represents alkyl or alkoxyalkyl.

2. A compound according to claim 1, in which
A represents fluorine or chlorine,
X represents oxygen or sulphur,
B represents hydrogen or $C_1$-$C_6$-alkyl,
$R^1$ represents hydrogen, $C_1$-$C_6$-alkyl, —COH or —CO—$C_1$-$C_6$-alkyl which is optionally substituted by halogen,
$R^2$ represents hydrogen or $C_1$-$C_6$-alkyl and
$R^3$ represents $C_1$-$C_4$-alkyl or $C_1$-$C_6$-alkoxy-$C_1$-$C_6$-alkyl.

3. A compound according to claim 1, in which
A represents fluorine or chlorine,
X represents oxygen or sulphur,
B represents hydrogen or $C_1$-$C_4$-alkyl
$R^1$ represents hydrogen, $C_1$-$C_4$-alkyl, —COH or —CO—$C_1$-$C_4$-alkyl which is optionally substituted by halogen,
$R^2$ represents hydrogen or $C_1$-$C_4$-alkyl and
$R^3$ represents $C_1$-$C_4$-alkyl or $C_1$-$C_4$-alkoxy-$C_1$-$C_4$-alkyl.

4. A compound according to claim 1, in which
A represents fluorine or chlorine,
X represents oxygen or sulphur,
B represents hydrogen,
$R^1$ represents hydrogen,
$R^2$ represents methyl or ethyl and
$R^3$ represents $C_3$-$C_4$-alkyl.

5. A compound according to claim 1, in which
X represents oxygen.

6. An insecticidal, acaricidal or nematicidal composition comprising an insecticidally, acaricidally or nematicidally effective amount of a compound according to claim 1 and a diluent.

7. A method of combating insects, acarids or nematodes which comprises applying to such insects, acarids or nematodes an insecticidally, acaricidally or nematicidally effective amount of a compound according to claim 1.

8. A compound of the general formula (XIV)

(XIV)

in which
A, B and X have the meaning given in claim 1,
$R^6$ represents halogen, —$SZ^1$ or —$SR^3$, in which $R^3$ has the meaning given in claim 1 and $Z^1$ represents one equivalent of an alkali metal ion, and
$R^7$ represents hlogen or

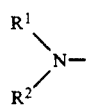

wherein $R^1$ and $R^2$ have the 1 meaning given in claim 1, with the provisos that
(a) $R^6$ and $R^7$ do not simultaneously denote halogen and
(b) $R^6$ represents halogen or $SZ^1$ if $R^7$ represents $R^1R^2$—N—.

* * * * *

UNITED STATES PATENT AND TRADEMARK OFFICE
CERTIFICATE OF CORRECTION

PATENT NO. : 5,166,144
DATED : November 24, 1992
INVENTOR(S) : Kruger et al.

It is certified that error appears in the above-identified patent and that said Letters Patent is hereby corrected as shown below:

Col. 17, line 8   After " $R_2$ " delete " represent " and substitute -- represents --

Col. 17, line 19  Delete " $C_1-C_4$-alkyl " and substitute -- $C_1-C_6$-alkyl --

Col. 18, line 33  After " the " delete " 1 "

Signed and Sealed this

Fourteenth Day of June, 1994

Attest:

BRUCE LEHMAN

*Attesting Officer*   *Commissioner of Patents and Trademarks*